US012686544B2

(12) United States Patent (10) Patent No.: US 12,686,544 B2
Astete Boettcher (45) Date of Patent: Jul. 21, 2026

(54) WATER-DEGRADABLE BAG

(71) Applicant: SOLUBAG SpA, Santiago (CL)

(72) Inventor: Roberto Astete Boettcher, Concepción (CL)

(73) Assignee: SOLUBAG SpA, Santiago (CL)

( * ) Notice: Subject to any disclaimer, the term of this patent is extended or adjusted under 35 U.S.C. 154(b) by 0 days.

(21) Appl. No.: 16/091,392

(22) PCT Filed: Jul. 25, 2017

(86) PCT No.: PCT/CL2017/000021
§ 371 (c)(1),
(2) Date: Jan. 25, 2019

(87) PCT Pub. No.: WO2018/018172
PCT Pub. Date: Feb. 1, 2018

(65) Prior Publication Data
US 2019/0152665 A1 May 23, 2019

(30) Foreign Application Priority Data

Jul. 25, 2016 (CL) .................................. 1885-2016

(51) Int. Cl.
B65D 65/46 (2006.01)
A61C 19/08 (2006.01)
(Continued)

(52) U.S. Cl.
CPC .............. B65D 65/46 (2013.01); A61C 19/08 (2013.01); A61G 1/01 (2013.01); A61L 31/06 (2013.01);
(Continued)

(58) Field of Classification Search
CPC ...... B65D 65/46; B65D 29/00; B65D 33/004; B65D 33/06; B65D 33/065; B65D 33/08;
(Continued)

(56) References Cited

U.S. PATENT DOCUMENTS

2003/0216098 A1* 11/2003 Carlyle ................ D04H 1/4309
156/62.4
2004/0216217 A1* 11/2004 Jones ..................... A41D 13/02
2/210
(Continued)

FOREIGN PATENT DOCUMENTS

CN 201647268 U 11/2010
GB 1047034 A 11/1966
(Continued)

OTHER PUBLICATIONS

16091392_Feb. 23, 2023_CN_201647268_U_M (Year: 2010).*
16091392_Jan. 25, 2024_JP_2000314067_A_M (Year: 2000).*

*Primary Examiner* — Nathan J Newhouse
*Assistant Examiner* — Nina K Attel
(74) *Attorney, Agent, or Firm* — ArentFox Schiff LLP

(57) ABSTRACT
This invention relates to a water-degradable flexible bag for carrying goods purchased from retailers or wholesalers, and/or for packing consumer goods or hygienic products, comprised of at least two parallel walls bonded in their upper section by at least one sealing band in each side edge, a sealing band bonding the lower ends of the parallel walls and an opening at the end, opposite to the sealing band, wherein each of the parallel walls consists of a nonwoven polyvinyl alcohol resin fabric. In a different embodiment, the invention also relates to a water-degradable flexible gurney cover for covering patient care gurneys, wherein said gurney cover consists of a nonwoven polyvinyl alcohol resin fabric.

14 Claims, 7 Drawing Sheets

(51) Int. Cl.

| | |
|---|---|
| *A61G 1/01* | (2006.01) |
| *A61L 31/06* | (2006.01) |
| *A61L 31/14* | (2006.01) |
| *B65D 30/00* | (2006.01) |
| *B65D 33/00* | (2006.01) |
| *B65D 33/06* | (2006.01) |
| *B65D 33/08* | (2006.01) |
| *B65D 33/10* | (2006.01) |
| *B65D 33/16* | (2006.01) |

(52) U.S. Cl.
CPC .............. *A61L 31/14* (2013.01); *B65D 29/00* (2013.01); *B65D 33/004* (2013.01); *B65D 33/065* (2013.01); *B65D 33/08* (2013.01); *B65D 33/105* (2013.01); *B65D 33/16* (2013.01)

(58) Field of Classification Search
CPC ...... B65D 33/10; B65D 33/105; B65D 33/12; B65D 33/02
See application file for complete search history.

(56)     References Cited

U.S. PATENT DOCUMENTS

| | | | | |
|---|---|---|---|---|
| 2005/0050608 A1* | 3/2005 | Jones | ...................... | G21F 9/001 |
| | | | | 2/102 |
| 2009/0196533 A1* | 8/2009 | Miwa | ...................... | A45C 3/04 |
| | | | | 383/7 |
| 2011/0312241 A1* | 12/2011 | Tang | ...................... | B32B 27/30 |
| | | | | 442/381 |
| 2014/0044380 A1* | 2/2014 | Weder | ................... | B65D 85/52 |
| | | | | 383/105 |
| 2014/0356597 A1* | 12/2014 | Steward | ................ | D21H 13/20 |
| | | | | 428/211.1 |

FOREIGN PATENT DOCUMENTS

| | | | |
|---|---|---|---|
| GB | 2267711 A | 12/1993 | |
| GB | 2530342 A | 3/2016 | |
| WO | WO-2015097101 A1 * | 7/2015 | ......... A45D 19/0066 |

\* cited by examiner

WATER-DEGRADABLE BAG

CROSS-REFERENCE TO RELATED APPLICATIONS

This application is a National Stage Entry of International Patent Application No. PCT/CL2017/000021, filed Jul. 25, 2017, which claims priority to Chilean Patent Application No. 1885-2016 filed Jul. 25, 2016. The entire contents of each of the priority applications are incorporated herein by reference.

This invention relates to a water-degradable flexible bag for carrying goods purchased from retailers or wholesalers, and/or for packing consumer goods or hygienic products, comprised of at least two parallel walls bonded in their upper section by their side edges, a sealing band bonding the lower ends of the parallel walls, and an opening at the end opposite to the sealing band, wherein the bag consists of a nonwoven polyvinyl alcohol resin fabric. In a different embodiment, the invention also relates to a water-degradable flexible gurney cover for covering patient care gurneys, wherein said gurney cover consists of a nonwoven polyvinyl alcohol resin fabric.

DESCRIPTION OF THE PRIOR ART

The daily use of plastic bags for carrying goods has become a major environmental problem, since said bags are still being widely used in countries with no regulation on the matter, resulting in a big accumulation of waste that will never degrade or will take hundreds of years to degrade; also known is the damage caused to the wildlife, especially marine wildlife, when plastic bags are thrown into the ocean, lakes or rivers as part of the regular household waste produced by human settlements.

Commercially used plastic bags became highly demanded when merchants found them to be a cost-effective solution for carrying their sold goods for a very low cost. The problem is increased when the quality of the plastic bags is so low that they cannot be used for a second time, since some of the bags currently produced are so thin that will immediately tear.

Another important factor to be taken into account is the recyclability of plastic bags, which is mentioned in some industries as a solution to the contamination problem caused by said bags; however, in reality, recycling is not an effective solution, since the costs of recycling plastic bags (high- or low-density polyethylene) is higher than the cost of the raw materials used in the fabrication of new bags, and therefore there is no technical or economic motivation for the tradi-tional plastic industry to start recycling bags.

The need for supplying means for carrying purchased goods or packing mass consumption products is undeniable, but since use of plastic bags is so high and widespread, there is also a need for them not to be a threat to the environment; therefore, solutions have been searched in the prior art aiming at the effective degradation of plastic bags, rather than promoting a better quality for their reutilization since ultimately, plastic bags will still be discarded and turn into waste.

Therefore, it is possible to find solutions that aim at reducing the life cycle of used plastic, resulting in their degradation time being reduced from hundreds of years to only one hundred years now. However, from an environ-mental point of view, while having the number of years necessary for plastic degradation reduced is an improve-ment, several years is still a very long time during which the bag can still cause damage, especially to marine wildlife species that are likely to swallow pieces of plastic, resulting in their dead.

Other improvements have been made in the development of new accelerated degradation materials that can be used in the manufacturing of objects such as bags; however, they have been proven to be ineffective due to their lack of strength or their high costs, which prevents them from competing with a bag made of traditional plastic, such as polystyrene, polyethylene, polypropylene, and other poly-meric materials.

Thus, the challenge is to achieve a material that allows enough thickness with a high tensile strength, requiring a simple production technology while allowing a total degra-dation of the material when it needs to be discarded, also not causing damage to the environment due to its degradation.

For this reason, efforts have been made to develop bio-degradable packing bags; however, degradable products are always, one way or another, structurally deficient due to their low resistance. Plastic materials made of petroleum-based polyolefin have been used as a carrier for the prepa-ration of degradable plastic, as also polylactic acid has been used; however, the low thermal resistance of the resulting material after the transformation, together with the relatively high cost of polylactic acid, make it not suitable for shop-ping bag requirements.

For example, CN Patent No. 103819803, by Huang Sheng, published on May 28, 2014, discloses a "Preparation method for degradable plastic for shopping bags", which describes the use of biodegradable polymeric materials obtained from the combination with natural materials such as starch and stearic acid, calcium stearate, calcium carbon-ate, liquid paraffin, high- and low-density polyethylene, ethyl-methyl acrylate copolymer, plus other coupling agents; however, the result is still not ideal, since the cost is too high and still uses contaminating materials that are not friendly to the environment.

Another similar example can be found in CN Patent No. 102875914, by Li Yin, published on Jan. 16, 2013, which refers to a degradable plastic bag that would not contaminate the environment. The technical solution of the degradable plastic bag is that it is formed using starch and polyvinyl chloride as raw materials. However, this solution does not achieve a good balance between its strength and its actual degradability at room temperature with no significant inter-vention.

On the other hand, the use of gurneys where patients or users can lie back, in doctor's offices or treatment rooms, is very common; typically, said gurneys are covered with a sheet of disposable paper, or "gurney cover" which, once used, is disposed in a waste bin (trash can) located next to the stretcher. Since said gurney cover must be removed after each patient, a large volume of paper can accumulate, hindering its later handling and final disposal.

For that reason, this invention overcomes the problems of the technique, proposing a bag for retail or wholesale shopping, which is easily degraded in water, at room tem-perature or hot, and is formed by a nonwoven polyvinyl alcohol resin fabric. Moreover, this invention overcomes another problem of the technique, proposing a disposable gurney cover for covering gurneys used for patient care, which is easily degraded in water, at room temperature or hot, and is formed by a nonwoven polyvinyl alcohol resin fabric.

This invention refers to plastic bags for carrying goods purchased from retailers or wholesalers, and/or packing consumer goods or hygienic products; wherein said bag can be made of a single piece between the body and the straps, such as the one described in U.S. Pat. No. 5,967,662, by Chew, published on Oct. 19, 1999, or made of one body plus added straps, such as the one shown in U.S. Pat. No. 3,490,682, by Schwarzkopf, published on Jan. 20, 1970; any other form of bag or packaging is also applicable under the concept of the invention that is the object of this application.

DESCRIPTION OF THE INVENTION

In order to better understand this invention, the following definitions must be provided:

Water-degradable: Material with the ability of completely degrading in water, whether cold or hot.

Sealing band: Section that bonds two sheets of materials, whether by thermal bonding, ultrasonic bonding, adhesive bonding, or seam bonding using natural or synthetic fibers. Wherein each band can have a width varying between 1-20 millimeters.

Gurney cover: Disposable sheet with a set length and width, used to cover gurneys on which patients or users lie back.

In a first embodiment, this invention refers to a bag for carrying goods purchased from retailers or wholesalers, and/or packing consumer goods or hygienic products, which is water-degradable in water at room temperature or hot water.

The bag is manufactured based on a melt-extruded fabric, such as a nonwoven fabric, and more specifically, the bag is made of a nonwoven, meltblown fabric comprising a polyvinyl alcohol resin that can dissolve in water at room temperature or hot water.

The polyvinyl alcohol is traditionally made by polymerization of vinyl acetate and subsequent hydrolyzation of the polymer into an alcohol. Polyvinylic alcohols vary in their polymerization degree and hydrolysis degree. The temperature at which polyvinylic alcohol dissolves can be varied by altering the orientation of the polymer, changing its hydrolysis degree, and its crystallization.

A nonwoven meltblown fabric is obtained in the same way as an nonwoven adhesive-bonded spunbond fabric, collectively known as meltblown-extrusion or meltblown spunbond. In the process, a melted polymer is extruded under pressure through the holes of a spunbonding nozzle, and then impacted by high-speed air which drags the filaments as they exit the matrix during the meltblown process. The energy in this stage is such that the diameter of the filaments formed is significantly reduced, and the filaments fracture resulting in microfibers of infinite length. This differs from the spunbonding process which preserves the continuity of the filaments. The process for forming either one layer or multiple layers of fabric is continuous; that is, the steps of the process are not interrupted by the extrusion of the filaments in order to form the first layer until the bonded band is rolled into a roll.

This nonwoven fabric can also be a layer within a construction consisting of several layers, which is why the fabric made of composed or laminated material is then consolidated, at least temporarily, generally through methods involving heat and pressure, such as thermal point bonding, so that the water-degradable bag that is the object of this application is comprised by at least two parallel walls bonded in their upper section by at least one sealing band on each of its side edges, a sealing band bonding the lower ends of the parallel walls, and an opening located at the upper end, opposite to the sealing band, wherein each of the parallel walls consists of a nonwoven polyvinyl alcohol resin fabric.

It within the scope of the present invention that the water-soluble meltblown fabric (nonwoven fabric) can be treated with an embossing or printing process, so as to generate a texture or appearance that is different on the fabric surface, of coarse type, allowing the incorporation of an area for information, such as advertisement, directions, decorations, etc., without the need of applying contaminating pigments or materials that are non-soluble or non-degradable in nature.

This coarse area can cover different regions of the bag, such as one or both outer faces of the bag, only the sealing band bonding the parallel walls that conform the bag, only a quarter of the bag walls, half of the bag walls, or the entire surface.

The water-degradable bag comprises central openings in its upper region that function as grab handles; a different option is that it has strap-like bands in its upper region which form openings that function as grab handles; or a pair continuous extension bands along the upper region of the parallel walls that form grab handles. Another option for the bag is that it has seals around its edges, but no handles. The bag can also make a packaging for consumer goods or hygienic products, such as covers for seat headrests in transportation vehicles.

The processes for producing plastic bags are widely known in the prior art, the variety of production processes known in the prior art are easily applicable for the production of the bags in this invention. Specific cases of production processes for plastic bags can be found in U.S. Pat. No. 4,362,526 (James R. Wilson), U.S. Pat. No. 5,967,662 (Yook-Meng Chew), and US 20020036148 (Richard A. Honstrater). The processes described in the above documents are completely applicable to the production of the plastic bag that is the object of this invention. The formation, on the bag, of the coarse region for incorporating advertisement or information, and also of the sealing bands where said information is incorporated, is achieved through an embossing technique, either hot or cold, which is produced using and appropriate embossing equipment that is attached to the machine where the bag is produced.

Notwithstanding the above, advertisement or information can also be incorporated only on the sealing bands of the bag; in this case, each sealing band is produced using an ultrasonic bonding technique, through which appropriate signs or symbols are also formed on the sealing band, resulting in information or advertisement aimed at the end user.

In a second embodiment of the bag disclosed herein, said bag can include a direct insertion of advertisement or information, either on the sheet itself or on the sealing bands, using a water-based flexographic printing so that when the bag is dissolved in water, no residues of contaminating paints remain in the dilution water.

In a third embodiment of the bag disclosed herein, said bag can be of different colors other than the basic color (white) so it is presented in a wide, appealing range of colors that make it attractive to the user. Said coloring is achieved incorporating the appropriate colorant to the basic mix, which can dissolve in water and does not leave any contaminating residues in the dissolution. Thus, the bag can be of different colors, such as: green, yellow, light blue and red, in their multiple shades.

Finally, a fourth embodiment of the present invention refers to a water-degradable flexible gurney cover, which can be used to cover gurneys used in the provision of medical care for patients or other users, which also consists of a nonwoven polyvinyl alcohol resin fabric.

DESCRIPTION OF THE FIGURES

The detailed description of the preferred embodiments of the invention patent will be presented together with the figures that are part of the present disclosure. It is important to point out that the figures are presented only as supporting elements for a better understanding of the invention, and they do not represent the flexible material bag nor the elements that form it, at a real or proportional scale. The invention can neither be limited to only what is shown in the figures, since they represent only the important elements of the invention and elements that are generally known in the prior art might not be included. Thus, Figures are as follows.

DETAILED DESCRIPTION OF THE INVENTION

The numbers for the components of the water-degradable bag remain unchanged, regardless of the type of bag illustrated in the different figures.

Figure 1:
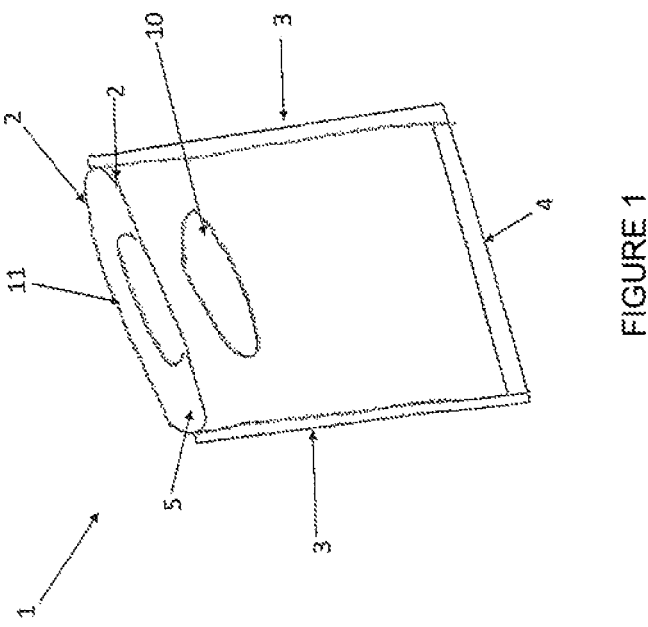
FIG. 1 shows an isometric view of the water-degradable bag based on an embodiment having a handle-type opening.

The present invention is related to a water-degradable flexible bag (1) for carrying goods purchased from retailers or wholesalers, and/or for packing consumer goods or hygienic products, wherein said bag, as shown in FIG. 1, consists of at least two parallel walls (2) bonded in their upper region by at least one sealing band (3) on each of its side borders; a sealing band (4) bonds the lower ends of the parallel walls, and an opening (5) located on the upper end, opposite to the lower sealing band (4), wherein each of the parallel walls (2) consists of a nonwoven polyvinyl alcohol resin fabric and comprises central openings (10) in its upper region which function as grab handles (11).

Figure 2:
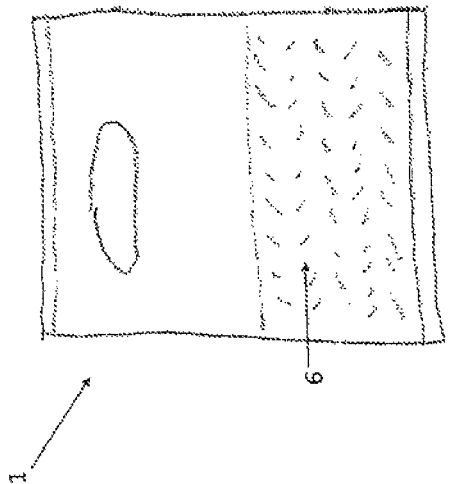
FIG. 2 shows a front view of the water-degradable bag based on an embodiment having a coarse region on one of its outer faces.
Figure 2:

As can be seen in FIG. 2, the bag (1) has a coarse region (6) for incorporating advertisement or information, wherein said coarse region (6) corresponds to an embossing or stamping on the fabric arranged on one of the outer faces of the bag, and that covers half of the height of the bag (1); but said coarse region can cover the entire height of the bag, or a third or a quarter of said height.

Figure 3:
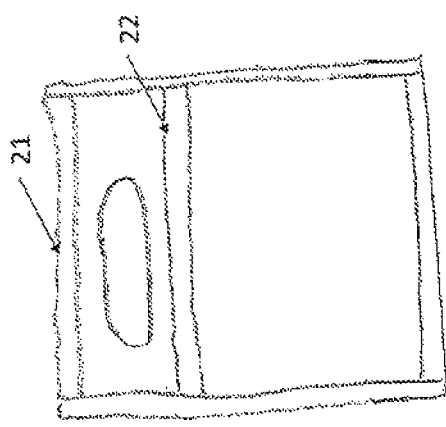
FIG. 3 shows a front view of the water-degradable bag, according to FIG. 1, based on an embodiment including side sealing bands, a seal band in the lower end, and sealing bands above and below the central opening.

Based on what can be seen in FIG. 3, the bag (1) comprises a band (21), along the full width of the bag, through the upper region of the central opening in each of the parallel walls; it can also include an intermediate band (22), along the full width of the bag, through the lower region of the central opening in each of the parallel walls; or it can also include a band, along the entire width of the bag, through the upper and lower regions of the central opening in each of the parallel walls.

Figure 4:
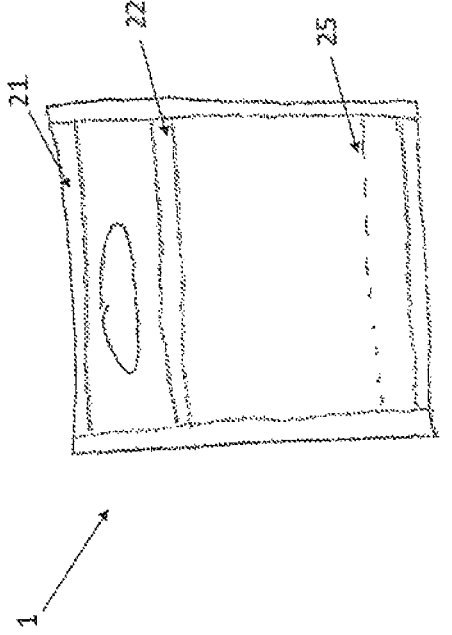
FIG. 4 shows a front view of the water-degradable bag, according to FIG. 3, based on an embodiment including an extensible crease between both parallel walls.

Based on what is illustrated in FIG. 4, the bag (1) includes an extensible crease (25) between both parallel walls, which acts as a gusset if necessary.

Figure 5:
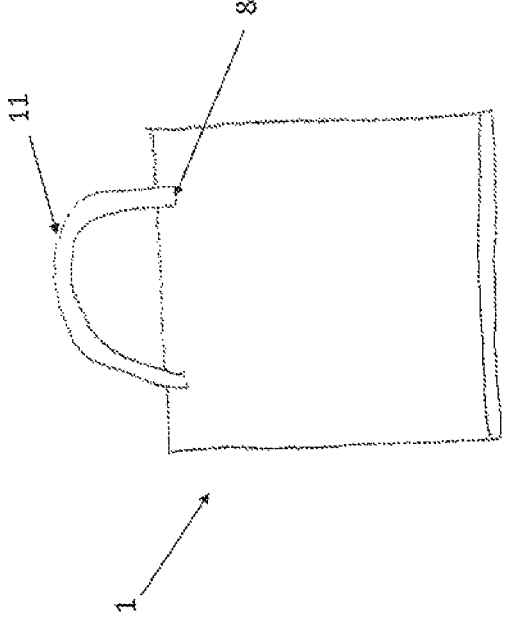
FIG. 5 shows a front view of the water-degradable bag based on an embodiment having handle-like added pieces.

FIG. 5 shows a water-degradable bag (1) comprising strap-like bands (8) in its upper region, forming openings that function as grab handles (11).

Figure 6:
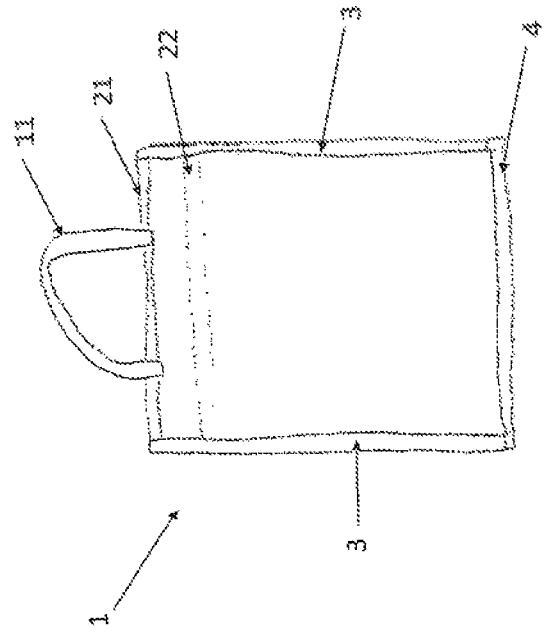
FIG. 6 shows a front view of the water-degradable bag, according to FIG. 5, based on an embodiment including side sealing bands, a seal band in the lower end, and an intermediate sealing band.

FIG. 6 shows a front view of the water-degradable bag (1), based on FIG. 5, wherein side sealing bands (3), a lower end sealing band (4), an upper band (21), and an intermediate band (22) are included.

Figure 7:
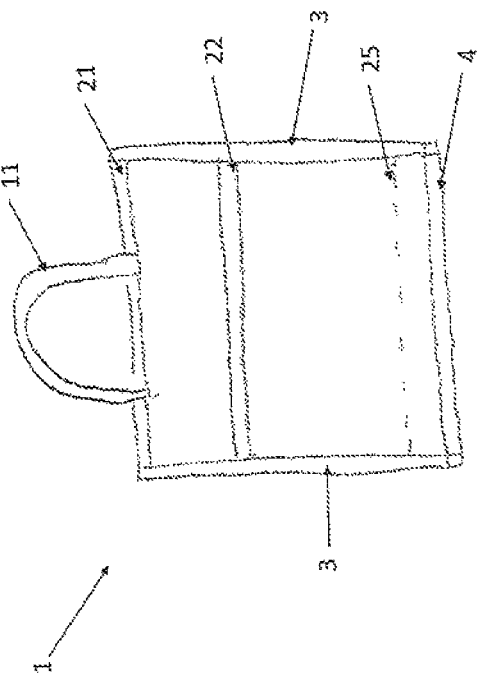
FIG. 7 shows a front view of the water-degradable bag, according to FIG. 6, based on an embodiment including an extensible crease between both parallel walls.

FIG. 7 shows a front view of the water-degradable bag (1), according to FIG. 6, including an extensible crease (25) between both parallel walls, which acts as a gusset if necessary.

Figure 8:
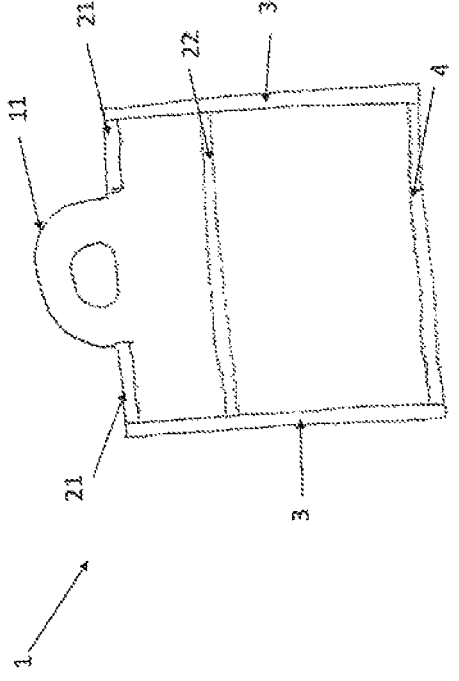
FIG. 8 shows a front view of the water-degradable bag, according to FIG. 6, based on an embodiment including handles that originate from the side walls themselves rather than from added pieces.

FIG. 8 shows a front view of the water-degradable bag (1), based on FIG. 6, including handles (11) that originate from the side walls, instead of stripe-like bands (8).

Figure 9:
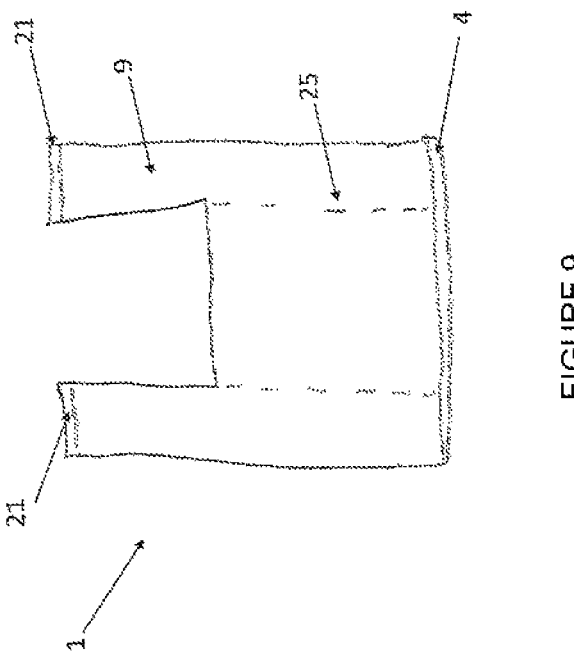
FIG. 9 shows a front view of the water-degradable bag, based on an embodiment including a pair of continuous extension bands along the upper region of the side walls.

FIG. 9 shows a front view of the water-degradable bag (1), including a pair of continuous extension bands (9) through the upper region of the parallel walls which form grab handles, a format usually known as "T-shirt bag". This type of bag incorporates two extensible creases (25) acting as gussets.

Figure 10:
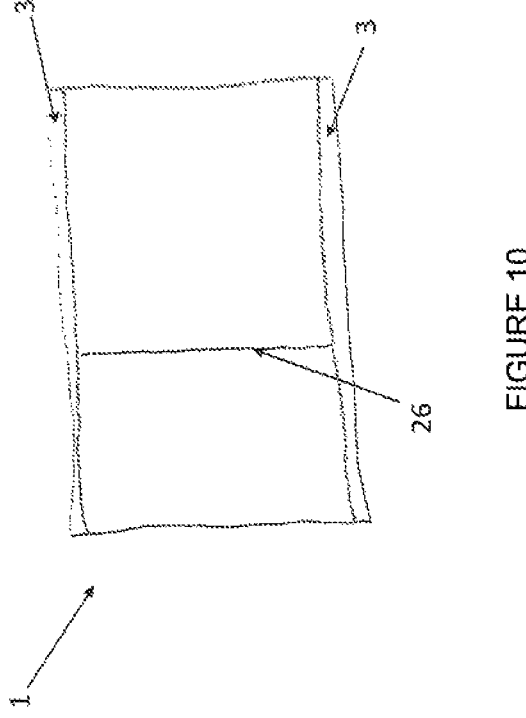
FIG. 10 shows a front view of the water-degradable bag, based on an embodiment forming a packaging.

FIG. 10 shows a front view of the water-degradable bag (1), which forms a packaging that can be adapted for wrapping consumer goods or hygienic products, such as covers for seat headrests in transportation vehicles. In this embodiment, the bag includes two side sealing bands (3), wherein the opening (26) for introducing the product is overlapped on a fraction of the actual packaging.

Figures 11, 12:
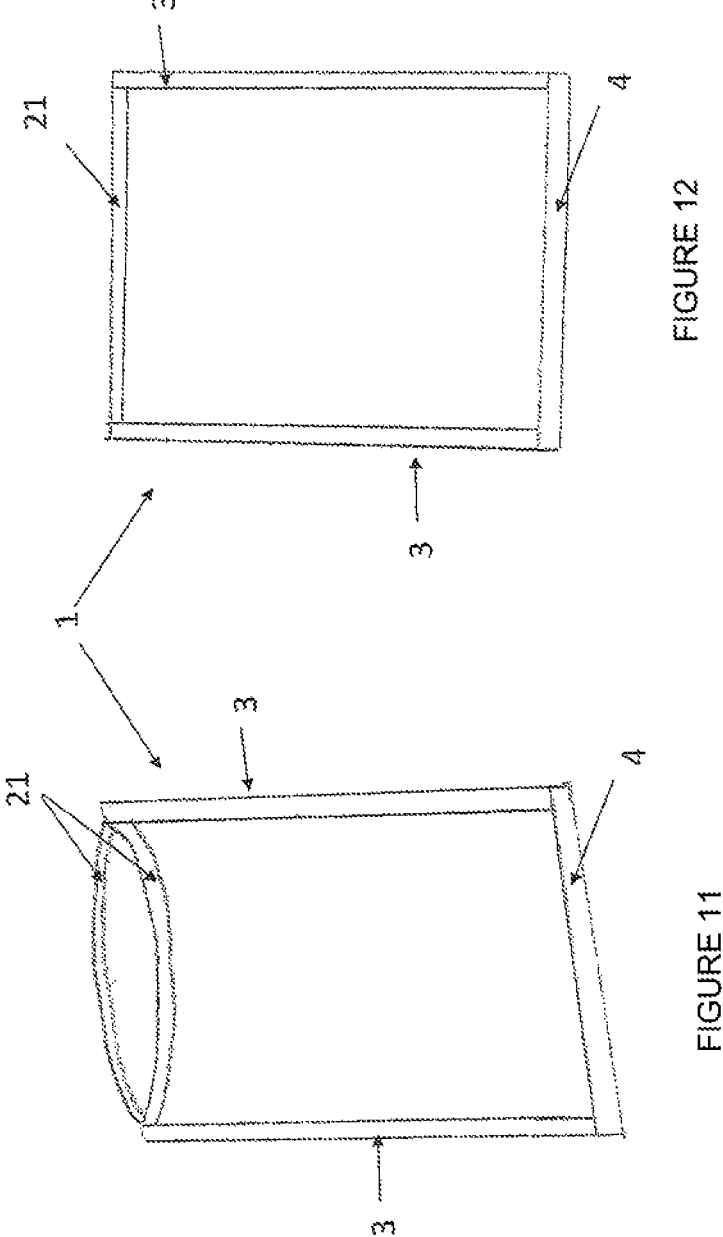
FIG. 11 shows an isometric view of the water-degradable bag, based on an embodiment not including grab handles.
FIG. 12 shows a front view of the water-degradable bag shown in FIG. 11.

FIG. 11 shows an isometric view of the type of water-degradable bag (1), according to the most basic embodiment of the present invention, which does not include grab handles but includes sealing bands all around the edges of the bag.

FIG. 12 shows a front view of the water-degradable bag (1) shown in FIG. 11, which includes side sealing bands (3), a lower sealing band (4) and an upper band (21).

It is important to point out that when the water-degradable bag (1) has an upper band (21) or an intermediate band (22), the actual band is located only on each side wall, not causing a bonding of the two side walls.

The water-degradable flexible bag, according to the present invention, as previously indicated, includes decorative figures or symbols, embossed, stamped and/or printed, which can be found on the coarse regions, and said coarse regions can correspond to the sealing bands or to a part or the entirety of one of the outer faces of the side walls, formed by a nonwoven polyvinyl alcohol resin fabric, that form the bag.

Figure 13:
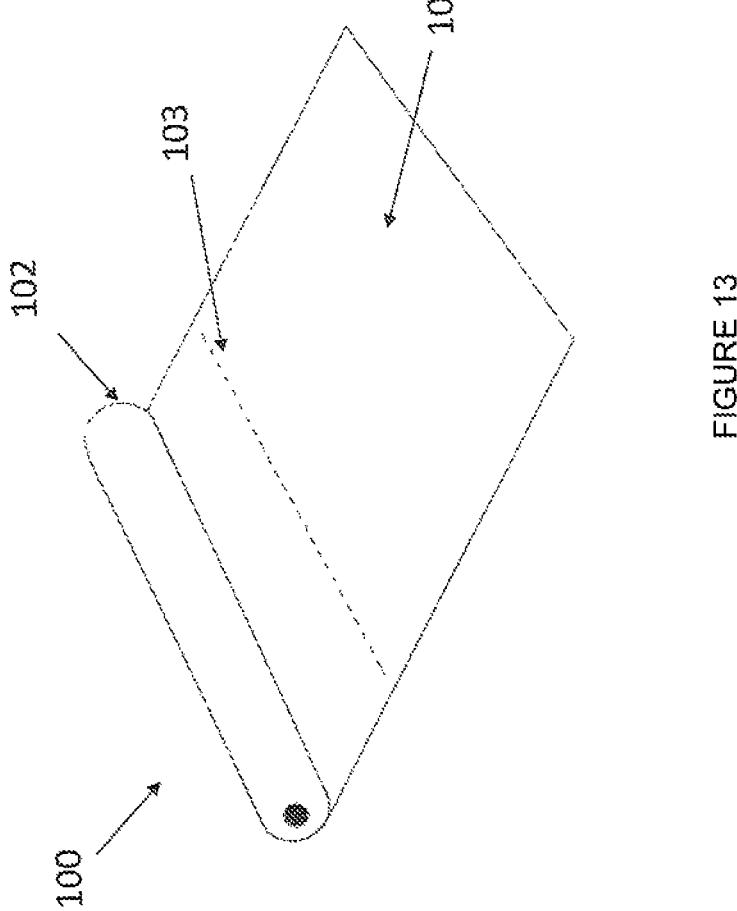
FIG. 13 shows an isometric view of the water-degradable flexible gurney cover, rolled and with its end spread out from the roll where it is held.

The water-degradable flexible gurney cover (100) embodiment illustrated in FIG. 13 is configured to be used for covering gurneys used for patient care, wherein said gurney cover (100) consists of a covering fabric made up of a nonwoven polyvinyl alcohol resin fabric. Originally, that is, before being used or spread out on a gurney, said gurney cover is presented as a continuous sheet (101) which is rolled, that is, in the shape of a roll (102), so that it can be extended on the gurney when it is going to be used. For easier removal of the gurney, the sheet (101) chat conforms the gurney cover (100) is perforated (103) widthwise and spaced in set in lengthwise segments. Thus, each sheet (101) of the gurney cover (100) can be perforated every 1 or 2 meters (3.3 and 6.6 feet), or in different set lengths. However, the gurney cover (100) can consist of one continuous sheet (101) with no perforation. The sheet that forms the water-degradable flexible gurney cover can have a width varying between approximately 50 centimeters (20 inches) and approximately 75 centimeters (30 inches).

For cases where it is specifically required or necessary, the water-degradable flexible gurney cover can consist of two or more sheets, wherein said sheets, after laminated, are rolled to form the roll that will be located in the end-user patient care facility.

The invention claimed is:

1. A water-degradable flexible bag for carrying goods purchased from retailers or wholesalers, or packing of consumer goods or hygienic products, comprising:

a first wall and a second wall parallel the first wall, each wall having an upper end, an upper section, a lower end, side edges, and an outer face, the first wall and the second wall being bonded together by at least one side sealing band on each of the side edges, a lower sealing band bonding the first wall to the second wall proximal the lower ends thereof, a region having a coarse texture for incorporating information thereupon located on at least one of the outer faces, and an opening located proximal to each upper end of each wall, opposite the lower sealing band, wherein the first wall, the second wall, the at least one side sealing band on each of the side edges, and the lower sealing band are formed from a material that consists of a nonwoven, meltblown fabric, wherein the nonwoven, meltblown fabric consists of a polyvinyl alcohol resin, wherein the polyvinyl alcohol resin is formed via polymerization of vinyl acetate to form a polymer and subsequent hydrolyzation of the polymer into an alcohol, and wherein each of the at least one side sealing band and the lower sealing band is provided by ultrasonic bonding.

2. The water-degradable flexible bag according to claim 1, wherein the region having the coarse texture corresponds to an embossing of the nonwoven, meltblown fabric.

3. The water-degradable flexible bag according to claim 1, wherein the region having the coarse texture corresponds to a stamping of the nonwoven, meltblown fabric.

4. The water-degradable flexible bag according to claim 1, wherein each of the side or the lower sealing bands have a width varying between 1 and 20 millimeters.

5. The water-degradable flexible bag according to claim 1, wherein the region having the coarse texture covers the lower sealing band at the lower end of the bag.

6. The water-degradable flexible bag according to claim 1, wherein the region having the coarse texture covers at least one of the side sealing bands at the side edges of the bag.

7. The water-degradable flexible bag according to claim 1, wherein the region having the coarse texture covers about a quarter of a height of the bag.

8. The water-degradable flexible bag according to claim 1, wherein the region having the coarse texture covers about half of a height of the bag.

9. The water-degradable flexible bag according to claim 1, wherein the region having the coarse texture covers an entire height of the bag.

10. The water-degradable flexible bag according to claim 1, wherein the bag comprises central openings in the upper section of each wall, which comprise grab handles.

11. The water-degradable flexible bag according to claim 1, wherein the bag comprises strap-like bands, the strap-like bands configured to form grab handles.

12. The water-degradable flexible bag according to claim 1, wherein the bag includes an extensible crease between both walls, the extensible crease configured to form a gusset.

13. The water-degradable flexible bag according to claim 12, wherein the extensible crease is arranged vertically or horizontally.

14. The water-degradable flexible bag according to claim 1, wherein the bag includes decorative figures or symbols, embossed, stamped or printed.

\* \* \* \* \*